US005464633A

United States Patent [19]

Conte et al.

[11] Patent Number: 5,464,633
[45] Date of Patent: Nov. 7, 1995

[54] PHARMACEUTICAL TABLETS RELEASING THE ACTIVE SUBSTANCE AFTER A DEFINITE PERIOD OF TIME

[75] Inventors: Ubaldo Conte, Busto Arsizio; Aldo La Manna; Lauretta Maggi, both of Pavia, all of Italy

[73] Assignee: Jagotec AG, Hergiswill, Switzerland

[21] Appl. No.: 248,232

[22] Filed: May 24, 1994

[51] Int. Cl.⁶ .............................. A61K 9/30; A61K 9/32; A61K 9/34; A61K 9/36

[52] U.S. Cl. .......................... 424/480; 424/474; 424/475; 424/476; 424/481; 424/482; 424/468

[58] Field of Search .................................. 424/464, 474, 424/475, 480, 482

[56] References Cited

U.S. PATENT DOCUMENTS 4,726,951  2/1988  Panoz et al. ............................ 424/465
4,756,911  7/1988  Drost et al. ............................ 424/468

OTHER PUBLICATIONS

Proced. Intern. Symp. Rel. Bioact. Mater., 12, pp. 45–46 (1985).
Techniques of Solubilization of Drugs, S. H. Yalkowsky, Ed. Marcel Dekker Inc. NY (1985) pp. 1,15,91, 135 & 159.
Diabetes, vol. 35, (1986) pp. 217–221.

Primary Examiner—Thurman K. Page
Assistant Examiner—James M. Spear

[57] ABSTRACT

Pharmaceutical tablets releasing the active substance after a definite period of time, consisting of: a core containing the active substance and polymeric substances which swell and/or gel and/or erode on contact with water or with aqueous liquids; a layer applied externally to said core, suitable to prevent the immediate release of the active substance contained in the core and to allow the release of said active substance after a definite period of time, consisting of natural and/or synthetic polymeric materials of the class of the hydrophilic polymers which erode and/or gel and/or dissolve in an aqueous medium; a possible gastroresistant and enterosoluble coating.

15 Claims, 1 Drawing Sheet

PHARMACEUTICAL TABLETS RELEASING THE ACTIVE SUBSTANCE AFTER A DEFINITE PERIOD OF TIME

PRIOR ART

Studies and researches for the preparation of systems and/or prototypes suitable to release an active substance in a controlled way have had a great impulse in recent years.

Said researches, which in the field of the pharmaceutical technology and in the biomedical field are generally indicated as "targeting", have the purpose of obtaining prototypes and/or therapeutic systems which release the active substance in a predeterminable way, for example the pharmaceutical form releases the active substance following changes of pH (in oral administrations of gastroresistant pharmaceutical forms) or following changes of temperature (for example as described in J. Controlled Release 4, 213, 1986 on thermoreversible hydrogels) or by effect of specific enzymes (for example as described in the documents of 12th Symposium on Controlled Release of Bioactive Materials—Geneve 1985 page 45) or by application of external means of activation such as the application of magnetic fields to open magnetized microcapsules or nanocapsules and/or the application of electric fields as in the recent applications of iontophoresis (as reported by Karl B., Diabetes 35, 217, 1986).

All said embodiments result somewhat complex and the preparation of prototypes and of systems having reproducible releasing characteristics is very difficult and, particularly in the case of the application of external activation, qualified operators and complex devices suitable to activate the system and to allow the active substance release, are necessary.

Regarding the treatment of chronical diseases which necessitate high drug doses, for example during the night time, pharmaceutical forms having a modified releasing (retard forms) and/or therapeutical systems having a high content of the active substance (from 2 to 5 times with respect to the content of the conventional pharmaceutical forms) suitable to release the active substance in a gradual way have been designed and commercialized.

Hydrophilic matrices possibly coated by permeable and/or semipermeable films are examples of such an embodiment.

In addition more complex pharmaceutical forms defined as therapeutic systems suitable to release the active substance at a constant rate have been produced. A typical example of said systems is the OROS system (described in "Formes Pharmaceutiques nouvelles" TEC-DOC Ed.—Paris 1985); such a system is commercially produced and largely used in the drug administration.

All said systems are designed to release the active substance in a regular and slow way obtaining plasmatic levels of the active substance for long times and for whole releasing time.

This fact leads to risks of collateral effects because the drug administration persists also when does not exist a therapeutical necessity in that the rise of the acute disease is due to very precise chronobiological rhythms as pointed out in the following.

The administration of high doses of drug for prolonged periods of time causes considerable collateral effects which, in the case of non-steroid antiinflammatory drugs, leads to the risk of serious gastric ulcerations and perforations.

In the case of OROS system based on indomethacin also lethal effects have been found (Remington's Pharmaceutical Sciences 18th ed. 1990 Mack Publishing Company, Easton, USA).

However all said embodiments, due to high content of the active substance, besides the risks of toxic effecs involve also the risk of the burst effect that is of releasing of the whole drug content of the pharmaceutical form in a short time and in addition they do not solve the problem of the necessity of a release temporally related to exacerbation of the pain or of the symptomatology to be cured.

However in the pharmaceutical-clinical practice there are several cases of diseases characterized in that the request of a therapeutically active substance is not constant for the time but obeys to circadian rhythms.

Therefore a release of the active substance in different times in a pulsatory way, for example some hours after administration, should be desirable.

Typical examples of such posology dosage schemes are well known for example in therapy of rheumatic diseases and/or of rheumatoid arthritis in which the patient shows an exacerbation of the painful symptomatology during the night and in the first hours in the morning when the effect of the administration of a traditional pharmaceutical form is already finished.

The necessity of a release of a drug after a definite period of time from the administration occurs in several pathological forms. For example in the arterial hypertension a pressure increase occurs in the first hours in the morning (when the patient is still sleeping); similarly in the asthmatic disease a symptomatology exacerbation during the night occurs. Particularly related to circadian rhythms are the angina pains (angina pectoris) which occur, with a repeatable regularity, at the end of the night period; a similar behaviour occurs in epileptic patients showing an exacerbated morbidity during the first hours in the morning.

A further disadvantage of the prior art consists in the effect of dose dumping particularly in the case of drugs largely soluble in aqueous liquids, that is in the releasing of a drug excess in a very short time which causes collateral effects not always easily supportable by the patient.

In view of overcoming said inconvenient several improvements have been carried out with the purpose to limit the release from hydrophilic matrices such as the whole coating by a semipermeable film suitable to limit the exit of the active substance from the pharmaceutical form.

A further improvement in the preparation of hydrophilic matrices is described in the U.S. Pat. No. 4,839,177 filed on 13 Jun. 1989 and in the Italian Application 22694-A/89 filed on 14 Dec. 1989 where a process is described having the purpose of limiting the releasing surface by partially coating the matrix surface by an impermeable film and/or by a polymeric material barrier which hinders the drug diffusion limiting its release to the free surface in contact with the dissolution medium.

Also in these embodiments the active substance release, although slowed down and without rising of burst effect, begins with a rate dependent on the formulation factors immediately after the immersion of the pharmaceutical form into the dissolution medium and/or immediately after the administration to the patient.

SUMMARY

We have now found, and constitutes an object of the present application for industrial invention, a new pharmaceutical tablet for oral administration suitable to release the active substance after a definite period of time from the administration.

Said pharmaceutical tablet consists of:

a core containing the active substance or substances to be released in the gastric or intestinal tract, polymeric substances which swell and/or gel and/or erode on contact with water or aqueous liquids and adjuvant and excipient substances normally used in the pharmaceutical technique;

a layer applied externally to said cope, preferably by compression, suitable to allow the release of the active substance or substances contained in the core after a definite period of time, and consisting of natural and/or synthetic polymeric materials of the class of hydrophilic polymers which erode and/or gel and/or dissolve in an aqueous medium and adjuvant and excipient substances normally used in the pharmaceutical technique. Such a layer does not contain active substance but acts only as a releasing modulator allowing the release of the active substance contained in the core after a definite period of time which can be controlled by proper in vitro tests;

a possible gastroresistant and enterosoluble coating applied on said external layer.

A new pharmaceutical form is obtained which does not release the active substance contained in the core fop a definite period of time. In fact the release of the active substance after administration of the pharmaceutical form occurs only when the characteristics of said external layer are modified by the contact with the gastro-intestinal liquids in such a way to allow the active substance dissolution. The finished pharmaceutical tablet (core+ external layer) can be coated with a film of gastroresistant polymeric material in such a way to allow the system activation only when the tablet attains the duodenal tract.

DETAILED DESCRIPTION OF THE INVENTION

The characteristics and advantages of the pharmaceutical tablets with release of the active substance after a definite period of time according to the present invention, will be pointed out to a greater extent duping the course of the following detailed description.

Said tablets consist of:

a core containing the active substance and polymeric substances swelling and/or gellable and/or erodible on contact with water or aqueous liquids and adjuvant substances;

a layer externally applied to said cope, able to prevent the immediate release of the active substance contained in the core and to allow the release of the said active substance after a definite period of time, consisting of natural and/or synthetic polymeric substances belonging to the class of the erodible and/or gellable and/or soluble in an aqueous medium hydropilic polymers and adjuvant substances;

a possible gastroresistant and enterosoluble coating.

BRIEF DESCRIPTION OF THE DRAWING

Said tablet has the form shown in FIG. 1, in which the cope is indicated by (1), the layer externally applied to the cope is indicated by (2) and the possible coating is indicated by (3).

The cope (1) is prepared by compression of the relative mixture possibly pregranulated, the layer (2) is preferably applied by compression of the relative mixture possibly pregranulated and the coating (3) is preferably applied by film-coating.

Figure 1:
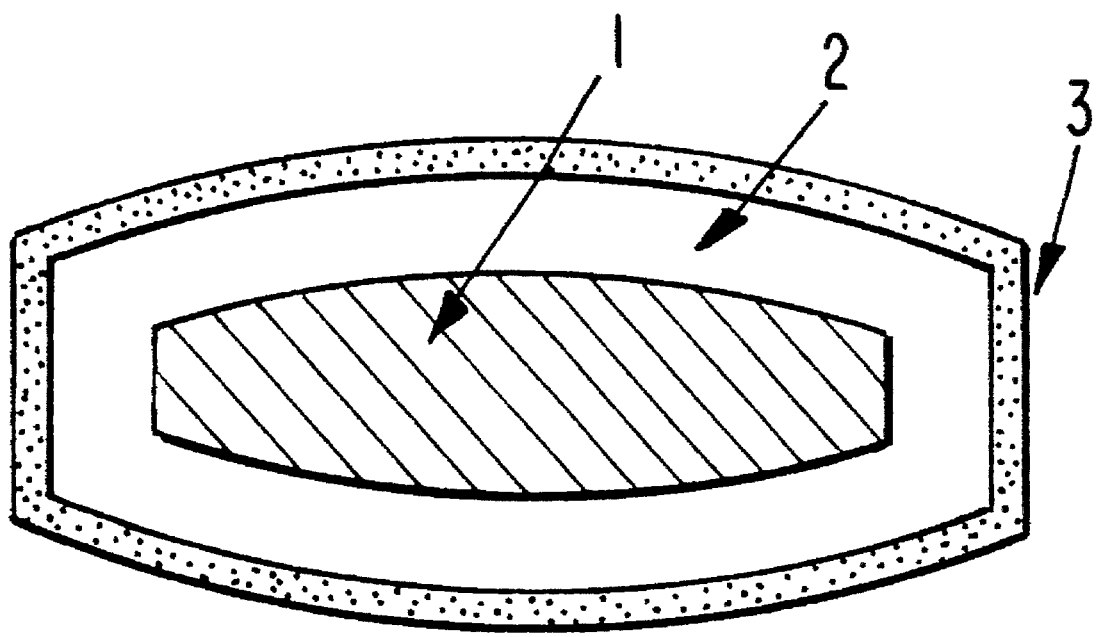

One of the characteristics of the tablet according to the invention consists in that in the preparation of the cope, in addition to the active substance, also polymeric substances able to modulate (to slow and/or to speed up) the release of the active substance, are used.

An active substance very soluble in water and/or aqueous liquids independently from the pH value of the dissolution medium and/or of the gastrointestinal tract may be used or an active substance poorly soluble in the same conditions, may be used. In this case particular adjuvants may be used to facilitate the quick dissolution as, for example, described in the volume "Techniques of Solubilization of Drugs" by S. H. Jalkowsky Ed.—M. Dekker New York 1985 and the Italian patent application No. 21091A/90 of 20 Jul. 90.

Non steroid (NSAID) or steroid antiinflammatory drugs as sodium diclofenac, indomethacin, ibuprofen, ketoprofen, diflunisal, piroxicam, naproxen, flurbiprofen, sodiun tolmetin, or sleep inductors and tranquillizers as diazepam, nitrazepam, flurazepam, oxazepam, chlordiazepoxide, medazepam, lorazepam or active substances for the prevention of angina attacks and hypertension as diltiazem, trapidil, urapidil, benziodarone, dipyridamole, lidoflazine, naphthydrofuryl oxalate, perhexiline maleate, oxyfedrine hydrocloride, or drugs of peptidic nature as insulin, calcitonin and somatostatin, may be used as active substances.

Crosslinked polyvinylpyrrolidone, hydroxypropylmethylcellulose, crosslinked sodium carboxymethylcellulose, carboxymethylstarch, potassium methacrylatedivinylbenzene, copolymer, polyvinylalcohols, starches, starch derivatives, betacyclodextrin and dextrins derivatives in general may be used, for example, as polymeric substances in the preparation of the said core. Said polymeric substances constitute from 1.0 to 90% of the core weight.

As far as the hydroxypropylmethylcellulose is concerned various types with different molecular weight (between 1,000 and 4,000,000) and with different substitution degree may be used.

Said types of hydroxypropylmethylcellulose present differentiated characteristics being mostly erodible or mostly gellable depending on the substitution degree (S.D.) shown in the polymer chain.

In addition adjuvant substances as natural and/or synthetic polymeric materials belonging to the class of the so called gellable hydrophilic polymers, able to slow the release of the active substance from the core, may be used.

Finally, excipients normally used in the pharmaceutical technique as mannitol, lactose, magnesium stearate, colloidal silica and others as glyceryl monostearate, hydrogensted castor oil, waxes, mono-bi-and trisubstituted glycerides, may be used.

When the penetration of the water and/or aqueous fluids in the core is to be helped, hydrophilic diluents as mannitol, lactose, starches of different origin, sorbitol and xylitol are introduced.

When the penetration of water and/or aqueous fluids in the core is to be slowed down, hydrophobic diluents as glyceryl monostearate, hydrogenated castor oil, waxes and mono-bi-trisubstituded glycerides are introduced. It is to remark that generally in the case of hydrophylic matrices, like those generally constituting the said core, particularly in the case of very soluble in aqueous liquids drugs, the "dose dumping" effect may occur, that is the release of an excessive amount of drug in a very short period of time, this fact causing the appearance of collateral effects not always easily tolerable by the patient.

The pharmaceutical tablets of the invention have the advantage of releasing the active substance contained in the core after a definite period of time and, containing a reduced amount of drug compared to the traditional retard forms, of avoiding the dose dumping effect.

Such result is reached by completely coating said core with an external layer, preferably but not necessarily, obtained by compression.

Said layer consists of natural and/or synthetic polymeric materials belonging to the class of the gellable hydrophilic polymers and/or to the class of the erodible hydrophilic polymers and/or gellable and soluble in water and/or in the dissolution medium at a rate which can be rigorously predetermined and controlled with proper tests in vitro, the rate of erosion and/or of dissolution being determined by all the substances constituting the formulation. In addition to said polymeric materials, excipients as hydrophilic agents, so called canalizing agents, may be used in the formulation used for said layer when the erosion or gelling or dissolution process is to be accelerated, or hydrophobic and water repellent agents when said process have to be slowed down.

Other technological adjuvants able to give to the material or to the mixture the suitable characteristics of industrial workability are moreover used.

The polymeric substances used in the preparation of the external layer, can show characteristics of gastroresistance and enterosolubility allowing the activation of the system only after the tablet has reached the enteric tract and in particular formulations of said polymeric substances able to obtain tablets expressly designed to the release of the active substance at the colon level, are possible.

The polymeric substances used for the external layer preparation are selected in the class comprising hydroxypropylmethylcellulose with a molecular weight between 1,000 and 4,000,000, hydroxypropylcellulose with a molecular weight between 2,000 and 2,000,000, carboxyvinyl polymers, polyvinylalcohols, glucans scleroglucans, mannans, xanthans, carboxymethylcellulose and derivatives, ethylcellulose, methylcellulose and, in general, cellulosic derivatives.

As far as the hydroxypropylmethylcellulose is concerned the remarks expressed on this substance in the use for the core preparation, are confirmed.

Said polymeric substances may be present in a percentage between 5 and 90 per cent of the total weight of said layer but preferably between 50 and 85 per cent.

Said polymeric substances, used one by one or mixed together, are able to determinate a "retard" in the release of the active substance contained in the core in a period of time between 15 minutes and more than 8 hours, also modifying the drug release rate from the core.

Said polymeric substances may be contained in the core too, when a slowed release of the active substance is to be obtained. Said external layer has a thickness between 0.2 and 4.5 mm if it is by compression applied and between 0.1 and 4.5 mm if it is by film-coating applied.

In the case said external layer is applied by compression diluents as those traditionally used in the solid forms preparation or fatty, waxy, natural and synthetic or semisynthetic substances as glyceryl monostearate and semisynthetic triglyceride derivatives, semisynthetic glycerides, hydrogenated castor oil, glycerylpalmitostearate, glyceryl behenate and other adjuvants such as binders as polyvinylpyrrolidone, gelatin, ethylcellulose, methylcellulose, sodium carboxymethylcellulose and other natural or synthetic substances well known to the skilled in the field, may be used.

For example magnesium stearate, stearic acid, sodium stearate, talc, sodium benzoate, boric acid, polyoxyethylenglycols and colloidal silica, are used.

Moreover diluent, lubricant, antiadherent and glidant substances, hydrophilic and canalizing agents and other substances able to give to said layer the requested characteristics can be used, as the following examples will better specify.

Said external layer may be obtained also by film-coating and/or lacquering process according to methods well known to the skilled in the field.

In such case besides the basic polymeric material as before described plasticizing substances as butylphthalate, propylphthalate, dietylphthalate, zein, polyoxyethylenglycols with different molecular weight and opacity agents as titanium dioxide and other adjuvants well known to the skilled in the field, may be used.

On said layer, independently from the ways of application, a film of gastroresistant and enterosoluble polymeric material can be further applied, to allow the system activation only after the tablet has reached the duodenum-intestinal tract.

Pharmaceutical systems of the last type may be used for the preparation of tablets specifically designed and adressed to release the active substance in the last part of the intestinal tract, that is at the colon level.

As polymeric materials to obtain the gastroresistance, cellulose, acetophthalate, cellulose acetopropionate, cellulose trimellitate, acrylic and methacrylic polymers and copolymers with different molecular weight and solubility dependent on different pH values may be used.

Said materials may be applied on the finished pharmaceutical form (core+external layer) by the classic film-coating process using solutions in organic solvents or aqueous dispersions and operating by nebulization in basin or in fluidized bed.

Said gastroresistant and enterosoluble materials may also be used in association with retarding polymers.

The following examples refer to the preparation of prototypes of the realization before described and they are reported only for explanatory and not limitative purpose of the present invention.

EXAMPLE 1

PREPARATION OF TRAPIDIL BASE TABLETS

1a—Preparation of the core granulate

N° 10.000 cores each having the following unit composition, are prepared:

| | |
|---|---|
| Trapidil (Inverni della Beffa, Milan, I) | 150.0 mg |
| Hydroxypropylmethylcellulose (Methocel K4, colorcon, Orpington, U.K.) | 30.0 mg |
| Mannitol (USP grade, C. Erba, Milan, I) | 98.3 mg |
| Polyvinylpyrrolidone (Plasdone ® K29-32, Gaf Corp., Wayne, NY, U.S.A.) | 3.7 mg |
| Magnesium stearate (USP grade, C. Erba Milan, I) | 2.0 mg |
| Colloidal silica (Syloid 244, Grace GmbH, Worms, D) | 1.0 mg |

The hydrophilic core manufacture process consists in the preparation of a granulate by mixing, in a sigma Erweka K5 type mod. (Frankfurt a.M. -D) mixer, the proper amounts of active substance, hydroxypropylmethylcellulose and mannitol; the homogeneous powder mixture is wetted with a 20% w/v alcoholic solution of polyvinylpyrrolidone and the mass is forced on a 25 mesh grid obtaining a regular granulate which is dried in a 40°–45 ° C. air circulation stove.

The granulate, dried to a constant weight, is placed in a Turbula T2A mod. (Bachofen—Basel—CH) powder mixer and added with magnesium stearate and colloidal silica and mixed for 20'.

The granulate, lubricated and analyzed for the active substance content, is submitted to the compression stage as forward described.

1b—Preparation of the granulate forming the external layer

The necessary amount of granulate for obtaining N° 10.000 external layers of 300 mg each having the following composition, is prepared.

| | |
|---|---|
| Hydroxypropylmethylcellulose (Methocel E 5 Premium, Colorcon, Orpington, U.K.) | 240.0 mg |
| Hydrogenated castor oil (Cutina HR, Henkel, Dussendorf, D) | 52.7 mg |
| Polyvinylpyrrolidone (Plasdone ® K29-32, Gaf Corp., Wayne, NY, U.S.A.) | 2.5 mg |
| Blue lacquer (Eigenmann - Veronelli, Milan, I) | 0.3 mg |
| Magnesium stearate (USP grade, C. Erba, Milan, I) | 3.0 mg |
| Colloidal silica (Syloid 244, Grace GmbH, Worms, D) | 1.5 mg |

The manufacture process consists in the preparation of a granulate by mixing in a sigma Erweka K5 type mod. (Frankfurt a.M. -D) mixer the proper amounts of hydroxypropylmethylcellulose, hydrogenated castor oil and blue lacquer; the homogeneous powder mixture is wetted with a 20% w/v alcoholic solution of polyvinylpyrrolidone and the mass is forced on a 25 mesh grid obtaining a regular granulate, of blue color, which is dried in a 40°–45° C. air circulation stove. The granulate, dried to a constant weight, is placed in a powder mixer (Turbula T2A mod.) and added with magnesium stearate and colloidal silica and mixed for 20'.

The granulate, lubricated, is submitted to the compression stage as forward described.

1c—Preparation of the finished tablets

For the preparation of the tablets as shown in FIG. 1 a Dry-Cota (Mannesty—Liverpool U.K.) rotating press machine is used; this machine, as it is known to the skilled in the field, consists of two coupled rotating presses of which the first for the core (1) manufacture and the second for the application of the external layer (2) by compression. A suitable system of transfer allows the correct location and centering of the core.

The machine is equipped with circular convex punchs (diameter=10.0 mm; R=10.0 mm) for the manufacture of the cores and of circular convex punchs (diameter=12.0; R=10.0 mm) for the application of the external layer.

In the present and in the following examples R indicates the bending radius of the punch.

The loading hopper of the first press is filled up with the granulate described at the point 1a while the two loading hoppers of the second press are filled up with the granulate described at the point 1b.

The first press is adjusted for producing 285 mg cores (equivalent to 150 mg of active substance) while the second one is adjusted for delivering an amount of granulate equivalent to 300 mg, for the external layer. With this amount an external layer of about 1.0 mm thickness is obtained.

Both said cores and the finished tablets are submitted to the dissolution test as below specified.

1d—Dissolution test

To estimate the releasing characteristics of the cores and of the finished (dry-coated) tablets, the equipment 1 described in USP XXII is used operating at 100 r.p.m. and using deionized water at 37° C. as dissolution fluid. The release of the active substance is controlled by U.V. spectrophotometric determination at 299 nm using a sampling and reading automatic system (Spectracomp 602 by Advanced Products—Milan).

The results of the tests are reported in the table 1.

TABLE 1

| Time (h) | Drug % released from the core without external layer | Drug % released from the finished tablet |
|---|---|---|
| 1 | 32.4 | 0.0 |
| 2 | 52.0 | 2.13 |
| 3 | 67.4 | 15.8 |
| 4 | 80.6 | 35.9 |
| 6 | 98.7 | 74.2 |
| 8 | 100.5 | 98.2 |
| 10 | | 99.8 |

It is possible to point out that the application of the external layer by the described technique causes a delay of about two hours in the appearance of the active substance in the dissolution medium and such behaviour quite corresponds to the aims of the present invention.

1e—Preparation of finished tablets with different thickness of the external layer The cores described at the point 1c are used but the press machine for the application of the external layer to said cores uses circular convex punchs of diameter=13.0 mm and R=10.0 mm; the machine is adjusted for producing an external layer of about 1.5 mm thickness, delivering a granulate amount of 400 mg.

Also in this case the finished 685 mg average weight tablets, are submitted to the dissolution test according to the point 1d. The obtained results, ever in comparison with the cores, are reported in the table II.

TABLE II

| Time (h) | Drug % released from the core without external layer | Drug % released from the finished tablet |
|---|---|---|
| 1 | 32.4 | 0.0 |
| 2 | 52.0 | 0.4 |
| 3 | 67.4 | 5.8 |
| 4 | 80.6 | 21.4 |
| 6 | 98.7 | 65.4 |
| 8 | 100.5 | 98.2 |
| 10 | | 99.4 |

Also in this case it is clear that the active substance release from the finished tablet begins only after a period of about two hours compared to the core without external layer.

This behaviour confirms the validity of the embodiment and points out how an even considerable change of the external layer, leads to a change in the "time-lag" of about 30–60 minutes confirming the security of the preparation because also important changes in weight and thickness of said layer allow to obtain comparable results.

EXAMPLE 2

PREPARATION OF SODIUM DICLOFENAC BASE TABLET

2a—Preparation of the core granulate

N° 10.000 cores, according to the following detailed way, each having the following unit composition, are prepared:

| | |
|---|---|
| Sodium diclofenac (Jago Pharma AG, Muttenz,CH) | 150.0 mg |
| Hydroxypropylmethylcellulose (Methocel K15 M. Colorcon, Orpington, U.K.) | 60.0 mg |
| Mannitol (USP grade, C. Erba, Milan, I) | 50.0 mg |
| Polyvinylpyrrolidone (Plasdone ® K29-32, Gaf Corp., Wayne, NY, U.S.A.) | 20.0 mg |
| Magnesium stearate (USP grade, C. Erba, Milan, I) | 3.0 mg |
| Colloidal silica (Syloid 244, Grace GmbH, Worms, D) | 2.0 mg |

The core manufacture process consists in the preparation of a granulate by mixing, in a sigma Erweka K5 type mod. (Frankfurt a.M. -D) mixer, the proper amounts of sodium diclofenac, hydroxypropylmethylcellulose and mannitol; the powder homogeneous mixture, is wetted with a 20% w/v alcoholic solution of polyvinylpyrrolidone and the mass is forced on a 25 mesh grid obtaining a regular granulate which is dried in a 40°–45° C. air circulation stove.

The granulate, dried to a constant weight, is placed in a Turbula T2A mod. (Bachofen—Basel—CH) powder mixer and added with magnesium stearate and colloidal silica and mixed for 20'.

The granulate, lubricated and analyzed for the active substance content, is submitted to the compression stage as forward described.

2b—Preparation of the granulate forming the external layer

A granulate having the same composition as reported in the former example 1b), is used.

2c—Preparation of the finished tablets

For the preparation of the tablets a Dry-Cota (Manesty—Liverpool U.K.) rotating press machine formerly described, is used. The machine is equipped with circular convex punchs (diameter=10.0 mm; R=10.0 mm) for the manufacture of the cores and with circular convex punchs (diameter= 12.0; R=10.0 mm) for the application of the external layer.

The first press is adjusted for producing 285 mg cores (equivalent to 150 mg of active substance) while the second one is adjusted for delivering an amount of granulate equivalent to 300 mg, for the external layer. With this amount an external layer of about 1.0 mm thickness is obtained.

Both said cores and the finished tablets are submitted to the dissolution test as below specified.

2d—Dissolution test

To estimate the releasing characteristics of the cores and of the finished tablets, the equipment 1 (described in USP XXII) is used operating at 100 r.p.m. and using deionized water at 37° C. as dissolution fluid. The release of the active substance is controlled by U.V. spectrophotometric determination at 276 nm using a sampling and reading automatic system (Spectracomp 602 by Advanced Products—Milan).

The results of the tests are reported in the table III.

TABLE III

| Time (h) | Drug % released from the core without external layer | Drug % released from the finished tablet |
|---|---|---|
| 1 | 18.6 | 0.0 |
| 2 | 32.1 | 0.9 |
| 3 | 44.3 | 7.7 |
| 4 | 55.7 | 18.9 |
| 6 | 76.9 | 43.6 |
| 8 | 98.0 | 66.3 |
| 10 | 100.3 | 90.1 |
| 12 | | 99.6 |

It is possible to point out that the application of the external layer causes a delay of about two/three hours in the appearance of the active substance in the dissolution medium and such behaviour quite corresponds to the aims of the present invention.

2e—Preparation of finished tablets with different thickness of the external layer The cores described at the point 2c) are used but the pressing machine for the application,by pressing, of the external layer to said cores uses circular convex punchs of diameter=13.0 mm and R=10.0 mm; the machine is adjusted for producing an external layer of about 1.5 mm thickness, delivering a granulate amount of 400 mg. Also in this case the finished 685 mg average weight tablets, are submitted to the dissolution test according to the point 2d.

The obtained results, ever in comparison with the copes, are reported in the table IV.

TABLE IV

| Time (h) | Drug % released from the core without external layer | Drug % released from the finished tablet |
|---|---|---|
| 1 | 18.6 | 0.0 |
| 2 | 32.1 | 0.3 |
| 3 | 44.3 | 3.2 |
| 4 | 55.7 | 13.3 |
| 6 | 76.9 | 35.8 |
| 8 | 98.0 | 60.1 |
| 10 | 100.3 | 81.6 |
| 12 | | 98.7 |

Also in this case it is clear that the sodium diclofenac release from the finished tablets begins only after a period of about two/three hours compared to the core without external layer.

EXAMPLE 3

PREPARATION OF KETOPROFEN BASE TABLETS

3a—Preparation of the core granulate

N° 10.000 cores, according to the following detailed ways, each having the following unit composition, are prepared:

| | |
|---|---|
| Ketoprofen (soc. Med. Scandicci, Firenze, I) | 150.0 mg |
| Maize starch (USP grade, C.Erba, Milan,I) | 120.0 mg |
| Polyvinylpyrrolidone (Plasdone ® K29-32, Gaf Corp., Wayne, NY, U.S.A.) | 2.0 mg |
| Crosslinked polyvinylpyrrolidone (Polylasdone XL ® Gaf Corp., Wayne, NY, U.S.A.) | 30.0 mg |
| Carboxymethylstarch (Explotab ®, Edward Mendell Co. Inc. Carmel, NY, U.S.A) | 28.0 mg |
| Magnesium stearate (USP grade, C. Erba Milan, I) | 1.5 mg |
| Colloidal silica (Syloid 244, Grace GmbH, Worms, D) | 0.5 mg |

The core manufacture process consists in the preparation of a granulate by mixing, in a sigma Erweka K5 type mod. (Frankfurt a.M. -D) mixer, the proper amounts of ketoprofen and maize starch; the omogeneous powder mixture is wetted with a 20% w/v alcoholic solution of polyvinylpyrrolidone and the mass is forced on a 25 mesh grid obtaining a regular granulate which is dried in a 40°–45° C. air circulation stove.

The granulate, dried to a constant weight, is placed in a Turbula T2A mod. (Bachofen—Basel—CH) powder mixer and crosslinked polyvinylpyrrolidone and carboxymethylstarch are added to the granulate and mixed for 20', magnesium stearate and colloidal silica are subsequently added and the granulate is mixed for further 20'.

The granulate, lubricated and analyzed for the active substance content, is submitted to the compression stage as forward described.

3b—Preparation of the granulate forming the external layer

A granulate having the same composition as reported in the former example 1b), is used.

3c—Preparation of the finished tablets

For the preparation of the ketoprofen base tablets the Dry-Cota (Mannesty—Liverpool U.K.) rotating press machine before described, is used.

The machine is equipped with circular convex punchs (diameter=10.0 mm; R=10.0 mm) for the manufacture of the cores and of circular convex punchs (diameter=12.0; R=10.0 mm) for the application of the external layer.

The machine is adjusted for producing 332 mg cores (equivalent to 150 mg of active substance) while it is adjusted for delivering an amount of granulate forming the external layer equivalent to 300 mg. Said amount allows to obtain an external layer of about 1.0 mm thickness.

Both said cores and the finished tablets are submitted to the dissolution test as below specified.

3d—Dissolution test

To estimate the releasing characteristics of both the cores and of the finished tablets, the equipment 1 (described in USP XXII) is used operating at 100 r.p.m. and using simulated intestinal fluid as dissolution fluid, pH=7.5 (according to USP XXII) without enzymes at 37° C. The release of the active substance is controlled by U.V. spectrophotometric determination at 262 nm using a sampling and reading automatic system (Spectracomp 602 by Advanced Products—Milan).

The results of the tests are reported in the table V.

TABLE V

| Time (min) | Drug % released from the core without external layer | Drug % released from the finished tablet |
|---|---|---|
| 3 | 100.2 | 0.0 |
| 60 | | 0.0 |
| 120 | | 0.0 |
| 150 | | 94.5 |
| 180 | | 99.8 |

It is possible to point out that the cores release the active substance in three minutes while, with the application of the external layer, the active substance is released only after a delay of about 120 minutes. Said behaviour quite corresponds to the aims of the present invention.

3e—Preparation of finished tablets with different thickness of the external layer The cores described at the point 3c) are used but the pressing machine for the application of the external layer to said cores uses circular convex punchs of diameter=13.0 mm and R=10.0 mm; the machine is adjusted for producing an external support of about 1.5 mm thickness, delivering a granulate amount of 400 mg.

Also in this case the finished 732 mg average weight tablets, are submitted to the dissolution test according to the point 3d.

The obtained results, ever in comparison with the cores, are reported in the table VI.

TABLE VI

| Time (min) | Drug % released from the core without external layer | Drug % released from the finished tablet |
|---|---|---|
| 3 | 100.2 | 0.0 |
| 60 | 0.0 | |
| 120 | 0.0 | |
| 180 | 84.2 | |
| 240 | 99.7 | |

Also in this case it is clear that the ketoprofen release from the finished tablet begins only after a period of about two/three hours compared to the core without external layer.

EXAMPLE 4

PREPARATION OF SODIUM DICLOFENAC BASE TABLETS

4a—Preparation of the core granulate

N° 10.000 cores, according to the following detailed ways, each having the following unit composition, are prepared:

| | |
|---|---|
| Sodium diclofenac (Jago Pharma AG,Muttenz,CH) | 150.0 mg |
| Hydroxypropylmethylcellulose (Methocel K15, Colorcon, Orpington, U.K.) | 60.0 mg |
| Mannitol (USP grade, C. Erba, Milan, I) | 50.0 mg |

-continued

| | |
|---|---|
| Polyvinylpyrrolidone (Plasdone ® K29-32, Gaf Corp., Wayne, NY, U.S.A.) | 20.0 mg |
| Magnesium stearate (USP grade, C. Erba Milan, I) | 3.0 mg |
| Colloidal silica (Syloid 244, Grace GmbH,Worms, D) | 2.0 mg |

The core manufacture process consists in the preparation of a granulate by mixing, in a sigma Erweka K5 type mod. (Frankfurt a.M. -D) mixer, the proper amounts of sodium diclofenac, hydroxypropylmethylcellulose and mannitol; the homogeneous powders mixture is wetted with a 20% w/v alcoholic solution of polyvinylpyrrolidone and the mass is forced on a 25 mesh grid obtaining a regular granulate which is dried in a 40°–45° C. air circulation stove.

The granulate, dried to a constant weight, is placed in a Turbula T2A mod. (Bachofen—Basel—CH) powder mixer and added with magnesium stearate and colloidal silica and mixed for 20'. The granulate, lubricated and analyzed for the active substance content, is submitted to the compression stage as forward described.

4b—Preparation of the granulate forming the external layer

The necessary amount of granulate for obtaining N° 10,000 external layers of 300 mg each having the following composition, is prepared.

| | |
|---|---|
| Hydroxypropylmethylcellulose (Methocel K4M Colorcon, Orpington, U.K.) | 135.0 mg |
| Mannitol (USP grade, C. Erba, Milan,I) | 135.0 mg |
| Polyvinylpyrrolidone (Plasdone ® K29-32, Gaf Corp., Wayne, NY, U.S.A.) | 24.6 mg |
| Red eudralack (E127, Biosintex, Milan, I) | 0.3 mg |
| Magnesium stearate (USP grade, C. Erba , Milan, I) | 3.0 mg |
| Colloidal silica (Syloid 244, Grace GmbH, Worms, D) | 1.5 mg |

The manufacture process consists in the preparation of a granulate by mixing in a sigma Erweka K5 type mixer the proper amounts of hydroxypropylmethylcellulose (in this case a high molecular weight and high viscosity K type hydroxypropylmethylcellulose is used, which forms a gellable instead of erodible barrier), mannitol and red lacquer; the homogeneous powder mixture is wetted with a 20% w/v alcoholic solution of polyvinylpyrrolidone and the mass is forced on a 25 mesh grid obtaining a regular granulate, of pink colour, which is dried in a 40°–45° C. air circulation stove. The granulate, dried to a constant weight, is placed in a powder mixer (Turbula T2A mod.) and added with magnesium stearate and colloidal silica and mixed for 20'.

The granulate, lubricated, is submitted to the compression stage as forward described.

4c—Preparation of the finished tablets

For the preparation of the tablets as shown in FIG. 1 a Dry-Cota (Mannesty—Liverpool U.K.) rotating press machine is used; said machine, as it is known to the skilled in the field, consists of two coupled rotating presses of which the first is assigned to cores (1) manufacture and the second to the application, by compression, of the external layer (2). A suitable system of "transfer" allows the correct location and centering of the core.

The used machine is equipped with circular convex punchs (diameter=10.0 mm; R=10.0 mm) for the manufacture of the cores and of circular convex punchs (diameter= 12.0; R=10.0 mm) for the application of the external layer.

The loading hopper of the first press is filled up with the granulate described at the point 4a while the two loading hoppers of the second press are Filled up with the granulate described at the point 4b.

The First press is adjusted for producing 285 mg cores (equivalent to 150 mg of active substance) while the second one is adjusted for delivering an amount of granulate equivalent to 300 mg, for the external layer. With this amount an external layer of about 1.0 mm thickness is obtained.

Both said copes and the finished tablets ape submitted to the dissolution test as below specified.

4d—Dissolution test

To estimate the releasing characteristics of the cores and of the finished (dry-coated) tablets, the equipment 1 described in USP XXII is used operating at 100 r.p.m. and using deionized water at 37° C. as dissolution fluid. The release of sodium diclofenac is controlled by U.V. spectrophotometric determination at 276 nm using a sampling and reading automatic system (Spectracomp 602 by Advanced Products—Milan).

The results of the tests are reported in the table VII.

TABLE VII

| Time (h) | Drug % released from the core without external layer | Drug % released from the finished tablet |
|---|---|---|
| 1 | 18.6 | 0.0 |
| 2 | 32.1 | 0.6 |
| 4 | 55.7 | 7.2 |
| 6 | 76.9 | 17.7 |
| 8 | 98.0 | 30.8 |
| 10 | 100.8 | 45.3 |
| 12 | | 59.4 |
| 14 | | 72.4 |
| 16 | | 86.6 |
| 18 | | 95.7 |
| 20 | | 98.6 |

It is possible to point out that the application of the external layer by the described technique causes a delay of about three/four hours in the appearance of the active substance in the dissolution medium and such behaviour quite corresponds to the aims of the present invention.

4e—Preparation of finished tablets with different thickness of the external layer The cores described at the point 4c) are used but the pressing machine for the application of the external layer to said cores uses circular convex punchs of diameter=13.0 mm and R=10.0 mm; the machine is adjusted for producing an external layer of about 1.5 mm thickness, delivering a granulate amount of 400 mg.

Also in this case the finished 685 mg average weight tablets, are submitted to the dissolution test according to the point -d. The obtained results, ever in comparison with the cores, are reported in the table VIII.

TABLE VIII

| Time (h) | Drug % released from the core without external layer | Drug % released from the finished tablet |
|---|---|---|
| 1 | 18.6 | 0.0 |
| 2 | 32.1 | 0.0 |
| 4 | 55.7 | 0.1 |
| 6 | 76.9 | 5.8 |
| 8 | 98.0 | 14.3 |
| 10 | 100.8 | 25.4 |
| 12 |  | 38.7 |
| 14 |  | 52.9 |
| 16 |  | 67.4 |
| 18 |  | 84.8 |
| 20 |  | 95.6 |

Also in this case it is clear that the active substance release from the finished tablet begins only after a period of about three/four hours compared to the core without external layer.

This behaviour confirms the validity of the embodiment and in this case points out that a change of the external layer leads to a change in the "time-lag" of about one/two hours compared to a lower thickness.

We claim:

1. Pharmaceutical tablet for oral administration suitable to release the active substance after a definite period of time, consisting essentially of:

a core containing the active substance to be released in the gastric or intestinal tract, a polymeric substance which swells and/or gels and/or erodes on contact with water or aqueous liquids and is selected from the group consisting of hydroxypropylmethylcellulose having a methoxyl content of 22.1% and a viscosity of 15,000 centipoises, crosslinked polyvinylpyrrolidone, crosslinked sodium carboxymethylcellulose, potassium methacrylate-divinyl-benzene copolymer, polyvinylalcohols and beta cyclodextrin and adjuvants and excipients;

a layer applied externally to said core by a compression process said layer being suitable to allow the release of the active substance contained in the core after a definite period of time and being selected from the group consisting of hydroxypropylmethylcellulose having a methoxyl content of 22.1 and a viscosity of 4,000 centipoises, carboxy vinyl polymers, glucans, mannans, xanthans and carboxymethylcellulose and adjuvants and excipients;

wherein said layer is applied externally to said core and has a thickness of 0.2–4.5 mm which allows the release of said active substance in said core after contact with water or an aqueous liquid for a period of 2 to 3 hours.

2. Tablet as claimed in claim 1, characterized in that said active substance is a non-steroid antiinflammatory drug or steroid antiiflammatory drug selected from the group consisting of sodium diclofenac, indomethacin, ibuprofen, ketoprofen, diflunisal, piroxicam, naproxen, flurbiprofen and sodium tolmetin.

3. Tablet as claimed in claim 1, characterized in that said active substance is a sleep inducer drug selected from the group consisting of diazepam, nitrazepam, flurazepam, oxazepam, chlordiazepoxide, medazepam and lorazepam.

4. Tablet as claimed in claim 1, characterized in that said active substance is an anti-hypertension drug selected from the group consisting of trapidil, urapidil, benziodarone, dipyridamole, diltiazem, lidoflazine, naphthydrofuryl oxalate, perhexiline maleate and oxyfedrine hydrochloride.

5. Tablet as claimed in claim 1, characterized in that said active substance is a peptide drug selected from the group consisting of insulin, calcitonin, and somatostatin.

6. Tablet as claimed in claim 1, characterized in that in said core composition said polymeric substances are contained in a percentage of from 1.0 to 90.0 of said core weight.

7. Pharmaceutical tablet for oral administration suitable to release a peptide drug selected from the group consisting of insulin, calcitonin and somatostatin after a definite period of time, said tablet consisting of:

core containing a peptide drug selected from the group consisting of insulin, calcitonin and somatostatin, a polymeric substance which swells and/or gels and/or erodes on contact with water or aqueous liquids and is selected from the group consisting of hydroxypropylmethylcellulose having a methoxyl content of 22.1% and a viscosity of 15,000 centipoises, crosslinked polyvinylpyrrolidone, crosslinked sodium carboxymethylcellulose, potassium methacrylate-divinyl-benzene copolymers, polyvinylalcohols and beta cyclodextrin and adjuvants and excipients;

a layer applied externally to said core by a compression process said layer being suitable to allow the release of said peptide drug contained in the core after a definite period of time and being selected from the group consisting of hydroxypropylmethylcellulose having a methoxyl content of 22.1 and a viscosity of 4,000 centipoises, carboxy vinyl polymers, glucans, mannans, xanthans and carboxymethylcellulose and adjuvants and excipients;

wherein said layer is applied externally to said core and has a thickness of 1.0–1.50 mm which allows the release of said active substance in said core after contact with water or an aqueous liquid for a period of 2 to 3 hours.

8. Tablet as claimed in claim 1, characterized in that said adjuvant substances of the core are hydrophilic diluents selected from the group consisting of mannitol, lactose, starches of different source, sorbitol, xylitol.

9. Tablet as claimed in claim 1, characterized in that said adjuvant substances of the core are hydrophobic diluents selected from the group consisting of glyceryl monostearate, hydrogenated castor oil, waxes and glycerides.

10. Pharmaceutical tablet for oral administration as defined in claim 1 wherein the external layer is about 1.0 mm to 1.5 mm thick.

11. Pharmaceutical tablet for oral administration as defined in claim 1 wherein the external layer is about 1.0 mm thick.

12. Pharmaceutical tablet for oral administration as defined in claim 1 wherein the external layer is about 1.5 mm thick.

13. Pharmaceutical tablet as claimed in claim 1, characterized in that said active substance is selected from the group consisting of diflunisal, piroxicam, flurbiprofen, sodium tolmetin, nitrazepam, flurazepam, oxazepam, chlordiazepoxide, medazepam, lorazepam, trapidil, urapidil, benziodarone, dipyridamole, diltiazem, lidoflazine, naphthydrofuryl oxalate, perhexiline maleate, oxyfedrine hydrochloride, insulin, calcitonin and somatostatin.

14. Tablet as claimed in claim 1, characterized in that said adjuvant and excipient substances used for the preparation of the external layer are selected from the group consisting of glyceryl monostearate, semisynthetic glycerides, hydrogenated castor oil, glyceryl palmitostearate, glyceryl behenate, polyvinyl pyrrolidine, gelatin, ethylcellulose, methylcellulose, sodium carboxymethylcellulose, magnesium stearate, stearic acid, sodium stearate, talc, sodium benzoate, boric acid, polyoxyethylene glycol and colloidal silica.

15. Pharmaceutical tablet for oral administration suitable to release the active substance after a definite period of time, consisting essentially of:

a core containing the active substance to be released in the gastric or intestinal tract, a polymeric substance which swells and/or gels and/or erodes on contact with water or aqueous liquids and is selected from the group consisting of hydroxypropylmethylcellulose having a methoxyl content of 22.1% and a viscosity of 15,000 centipoises, crosslinked polyvinylpyrrolidone, crosslinked sodium carboxymethylcellulose, potassium methacrylate-divinyl-benzene copolymer, polyvinylalcohols and beta cyclodextrin and adjuvants, and excipients;

a layer applied externally to said core by a compression process said layer being suitable to allow the release of the active substance contained in the core after a definite period of time and being selected from the group consisting of hydroxypropylmethylcellulose having a methoxyl content of 22.1 and a viscosity of 4,000 centipoises, carboxyl vinyl polymers, glucans, mannans, xanthans and carboxymethylcellulose and adjuvants and excipients;

wherein said layer is applied externally to said core and has a thickness of 0.2–4.5 mm which allows the release of said active substance in said core after contact with water or an aqueous liquid for a period of 2 to 3 hours wherein said pharmaceutical tablet has a gastroresistant and enterosoluble coating which consists of polymeric materials selected from the group consisting of cellulose acetophthalate, cellulose acetopropionate, cellulose trimellitate, acrylic polymers, acrylic copolymers, methacrylic polymers and methacrylic copolymers.

* * * * *